(12) United States Patent
Yamada

(10) Patent No.: US 7,884,116 B2
(45) Date of Patent: Feb. 8, 2011

(54) OCTAHYDRONAPHTHALENE DERIVATIVE AND MEDICINE

(75) Inventor: Naoyoshi Yamada, Kasatsu (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 356 days.

(21) Appl. No.: 10/596,827

(22) PCT Filed: Dec. 24, 2004

(86) PCT No.: PCT/JP2004/019402

§ 371 (c)(1),
(2), (4) Date: Jun. 26, 2006

(87) PCT Pub. No.: WO2005/070856

PCT Pub. Date: Aug. 4, 2005

(65) Prior Publication Data

US 2007/0142539 A1    Jun. 21, 2007

(30) Foreign Application Priority Data

Dec. 26, 2003    (JP)    ............................. 2003-435677

(51) Int. Cl.
*A61K 31/4425* (2006.01)
*C07D 213/56* (2006.01)
(52) U.S. Cl. ........................ 514/357; 546/337
(58) Field of Classification Search ................ 546/264, 546/337; 514/332, 357
See application file for complete search history.

(56) References Cited

FOREIGN PATENT DOCUMENTS

JP    7-179391 A    7/1995

OTHER PUBLICATIONS

Buckanovich et al., "Endothelin B receptor, etc.," Nature Medicine, Jan. 14, 2008, 28-36.*
Huang et al., "Increased ICAM-1, etc." Medline 1098387, 2001.*
Kobayashi et al., "Endothelail Cell, etc.," Current Medicinal Chemistry, 2007, 14, 377-386.*
Patarroyo, Manuel, et al., "Leucocyte Adhesion to Cells in Immune and Inflammatory Responses," The Lancet, 2(8672), Nov. 11, 1989, p. 1139-1142.
Dustin, Michael L., et al., "Role of Lymphocyte Adhesion Receptors in Transient Interactions and Cell Locomotion," Annual Review of Immunology, vol. 9, 1991, p. 27-66.
Springer, Timothy A., et al., "Adhesion Receptors of the Immune System," Nature, vol. 346, Aug. 2, 1990, p. 425-434.
Diamond, Michael S., et al., "ICAM-1 (CD54): A Counter-Receptor for Mac-1 (CD11b/CD18)," Journal of Cell Biology, vol. 111, No. 6 (pt. 2), Dec. 1990, p. 3129-3139.
Rosenstein, Yvonne, et al., "CD43, A Molecule Defective in Wiskott-Aldrich Syndrome, Binds ICAM-1," Nature, vol. 354, Nov. 21, 1991, p. 233-235.
Iigo, Yutaka, et al., "ICAM-1-Dependent Pathway is Critically Invloved in the Pathogenesis of Adjuvant Arthritis in Rats," The Journal of Immunology, vol. 147, No. 12, Dec. 15, 1991, p. 4167-4171.
Kavanaugh, Arthur F., et al., "Treatment of Refractory Rheumatoid Arthritis with an Anti-CD54 (Intercellular Adhesion Molecule-1, ICAM-1) Monolonal Antibody," Arthritis Rheum., 1992, vol. 35 (supplement), No. 53.
Kawasaki, Katsutoshi, et al., "Antibodies Against Intercellular Adhesion Molecule-1 and Lymphocyte Function-Associated Antigen-1 Prevent Glomerular Injury in Rat Experimental Crescentic Glomerulonephritis," The Journal of Immunology, vol. 150, No. 3, Feb. 1, 1993, p. 1074-1083.
Cosimi, A. Benedict., et al., "In Vivo Effects of Monoclonal Antibody to ICAM-1 (CD54) in Nonhuman Primates with Renal Allografts," The Journal of Immunology, vol. 144, No. 12, Jun. 15, 1990, p. 4604-4612.
Barton, Randall W., et al., "The Effect of Anti-Intercellular Adhesion Molecule-1 on Phorbol-Ester-Induced Rabbit Lung Inflamation," The Journal of Immunology, vol. 143, No. 4, Aug. 15, 1989, p. 1278-1282.
Seko, Yoshinori, et al., "Expression of Intercellular Adhesion Molecule-1 in Murine Hearts with Acute Myocarditis Caused by Coxsackievirus B3," J. Clin. Invest., vol. 91, Apr. 1993, p. 1327-1336.
Wegner, Craig D., et al., "Intercellular Adhesion Molecule-1 (ICAM-1) in the Pathogenesis of Asthma," Science, vol. 247, 1990, p. 456-459.
Wallace, John L., et al., "Role of Endothelial Adhesion Molecules in NSAID-induced Gastric Mucosal Injury," American Journal of Physiology, vol. 265, 1993, p. G933-998.
Ondeyka, John G., et al, Coprophilin: An Anticoccidial Agent Produced by a Dung Inhabiting Fungus, Biooganic & Medicinal Chemistry Letters, 1998, vol. 8, No. 24, pp. 3439-3442.

* cited by examiner

*Primary Examiner*—Patricia L Morris

(57) ABSTRACT

It is an object of the invention to provide a novel octahydronaphthalene derivative with an activity of inhibiting ICAM-4 expression and a pharmaceutically acceptable salt thereof. The invention encompasses, for example, agents for suppressing ICAM-1, therapeutic agents for inflammatory diseases, therapeutic agents for rheumatoid arthritis, immunosuppressive agents, and agents for suppressing cell growth, comprising N-(pyridin-3-ylmethyl)-(2E,4E)-5-[(1S,2S,4aR, 6R,7S,8S,8aS)-7-hydroxy-2,6,8-trimethyl-1,2,4a,5,6,7,8,8a-octahydronaphthalen-1-yl]-2-methylpenta-2,4-dienamide as an active ingredient.

4 Claims, 6 Drawing Sheets

→ NOE

OCTAHYDRONAPHTHALENE DERIVATIVE AND MEDICINE

CROSS-REFERENCE TO PRIOR APPLICATION

This is a U.S. National Phase Application under 35 U.S.C. §371 of International Patent Application No. PCT/JP2004/019402 filed Dec. 24, 2004, and claims the benefit of Japanese Patent Application No. 2003-435677 filed Dec. 26, 2003 both of which are incorporated by reference herein. The International Application was published in Japanese on Aug. 4, 2005 as WO 2005/070856 A1 under PCT Article 21(2).

TECHNICAL FIELD

The present invention relates to an octahydronaphthalene derivative or a pharmaceutically acceptable salt thereof, and a pharmaceutical composition containing an octahydronaphthalene derivative or a pharmaceutically acceptable salt thereof as an active ingredient.

BACKGROUND OF THE INVENTION

Cell adhesion molecules are a group of molecules existing on cellular surface and mediating the adhesion between a cell and a cell and between cell and extracellular matrix. The phenomenon called adhesion through adhesive molecules is involved not only in cell adhesion but also in cellular information transmission and activation, and plays an important role in biological defense reactions mainly including inflammation and immune reaction. Inflammatory leukocyte playing an important role in inflammation adheres to cell adhesion molecules expressed in vascular endothelium, and subsequently passes through in between vascular endothelial cells to infiltrate into an inner tissue. Then the inflammatory leukocyte releases various inflammatory mediators and the like, so that the leukocyte plays an important role in the onset and invasion of inflammation. Currently, the presence of various cell adhesion molecules is known. Among these, ICAM-1 (intercellular adhesion molecule-1) is significantly expressed in the vascular endothelium in which inflammation is caused. Therefore, it is suggested that ICAM-1 is highly involved therein (see, for example, non-patent reference 1).

As T cell receptors, CD4, CD8, and VCAM-1 (vascular cell adhesion molecule-1), ICAM-1 is a cell adhesion molecule belonging to the immunoglobulin super family, and is a protein of 76 to 114 kDa, which depends on the difference in the sugar chain added. ICAM-1 was considered as a ligand of LFA-1 (lymphocyte function-associated antigen-1) at an early stage (see, for example, non-patent references 2 and 3). Subsequently, it was revealed that the molecule worked as ligands of Mac-1 and CD43 (see, for example, non-patent references 4 and 5).

Examinations using various animal models indicate that a therapeutic treatment using anti-ICAM-1 antibodies is effective not only for rheumatoid arthritis (see, for example, non-patent references 6 and 7) but also for glomerular nephritis (see, for example, non-patent reference 8), rejections in organ grafting (see, for example, non-patent reference 9), pneumonia (see, for example, non-patent reference 10), myocarditis (see, for example, non-patent reference 11), asthma (see, for example non-patent, reference 12), and ulcer (see, for example, non-patent reference 13). Thus, it is suggested that there is a possibility that the therapeutic treatment of various diseases can be achieved by controlling the expression of ICAM-1.

Antisense and antibodies against ICAM-1 have been developed so far as therapeutic agents and immunosuppressive agents of rheumatoid and inflammatory diseases. However, none of such agents have been introduced on market yet. Therefore, creation of a novel therapeutic agent for inflammatory diseases with a novel activity mechanism has been desired.

It is reported that Coprophilin represented by the following formula (2) has an antibacterial activity. However, there has been no description about an activity of suppressing ICAM-1 expression, an anti-inflammatory activity, an immunosuppressive activity and an activity of suppressing cell growth (see, for example, non-patent reference 14).

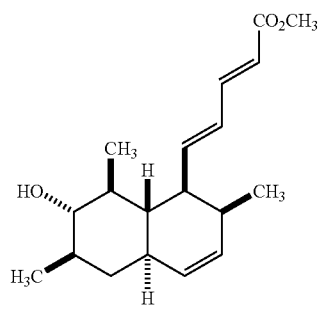

[2]

Non-patent reference 1: Patarroyo M, et al.: Lancet., 1989, Nov. 11, 2(8672), 1139-42.

Non-patent reference 2: Dustin M L, et al.: Annu. Rev. Immunol., 1991, 9, 27-66

Non-patent reference 3: Springer T A: Nature, 1990, 346, 425-434

Non-patent reference 4: Diamond M S, et al.: J. Cell Biol., 1990, 111, 3129-3139

Non-patent reference 5: Rosenstein Y, et al.: Nature, 1991, 354, 233-235

Non-patent reference 6: Iigo Y, et al.: J. Immunol., 1991, 147, 4167-4171

Non-patent reference 7: Kavanaugh A F, et al.: Arthritis. Rheum., 1992, 35(Sppul.), 53

Non-patent reference 8: Kawasaki K, et al.: J. Immunol., 1993, 150, 1074-1083

Non-patent reference 9: Cosimi A B, et al.: J. Immunol., 1990, 144, 4604-4612

Non-patent reference 10: Barton R W, et al.: J. Immunol., 1989, 143, 1278-1282

Non-patent reference 11: Seko Y, et al.: J. Clin. Invest., 1993, 91, 1327-1336

Non-patent reference 12: Wegner C D, et al.: Science, 1990, 247, 456-459

Non-patent reference 13: Wallance J L, et al.: Am. J. Physiol., 1993, 265, G933-998

Non-patent reference 14: Ondeyka J G, et al.: Bioorg. Med. Chem. Lett., 1998, 8, 3439-3442

DISCLOSURE OF THE INVENTION

An object of the invention is to provide a novel octahydronaphthalene derivative having an inhibitory activity of ICAM-1 expression and a pharmaceutically acceptable salt thereof. Another object of the invention is to provide an octahydronaphthalene derivative having an activity of suppressing cell growth and a pharmaceutically acceptable salt thereof.

Means for Solving the Problems

As the results of the intensive investigations, the inventor found that an octahydronaphthalene derivative of the invention and a pharmaceutically acceptable salt thereof could attain the objects. Thus, the invention has been achieved.

The invention relates to an octahydronaphthalene derivative represented by the following formula (1):

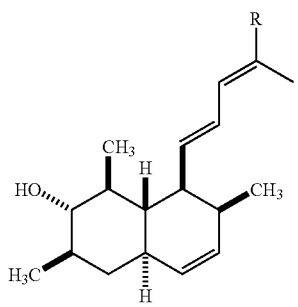

[1]

wherein R represents carboxy, hydroxymethyl, alkoxymethyl, alkoxycarbonyl, or —$CONR^1R^2$;

$R^1$ and $R^2$ are the same or different and each represents a hydrogen atom, phenyl, or alkyl, and wherein said alkyl may be substituted by 1) phenyl which may be substituted by a halogen atom, alkyl, dialkylamino, hydroxyl, or alkoxy;

2) 2-pyridyl;

3) 3-pyridyl; or 4) 4-pyridyl, or a pharmaceutically acceptable salt thereof.

Among the above octanaphthalene derivatives, N-(pyridin-3-ylmethyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide is preferable.

Additionally, the invention relates to a pharmaceutical composition containing a compound of the invention as an active ingredient, such as an agent for inhibiting ICAM-1 expression, a therapeutic agent for inflammatory diseases, an immunosuppressive agent, and an agent for suppressing cell growth. Specifically, examples thereof may include a therapeutic agent for rheumatoid arthritis and an anti-cancer agent.

The invention is now described below in detail.

Examples of "alkyl" according to the invention may include linear or branched alkyl having 1 to 10 carbon atoms such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, n-nonyl and n-decyl. Particularly, the alkyl is preferably a linear alkyl having 1 to 3 carbon atoms.

The alkyl moiety in "dialkylamino", "alkoxy", "alkoxymethyl", and "alkoxycarbonyl" includes the alkyls described above.

Examples of "halogen" may include fluorine, chlorine, bromine and iodine.

"An agent for suppressing ICAM-1 expression" means a pharmaceutical agent suppressing the expression of ICAM-1 which is one of the cell adhesion molecules. Specifically, Examples thereof may include therapeutic agents for inflammatory diseases and immunosuppressive agents.

"A therapeutic agent for inflammatory diseases" is not limited as long as it is an agent for diseases involving inflammation. Examples thereof may include therapeutic agents for diseases involving inflammation, such as rheumatoid arthritis, glomerular nephritis, pneumonia, myocarditis, asthma, and ulcer.

"An agent for suppressing cell growth" means a pharmaceutical agent for therapeutically treating various diseases by suppressing cell growth and example thereof include an anti-cancer agent.

BEST MODE FOR CARRYING OUT THE INVENTION

Figure 1:
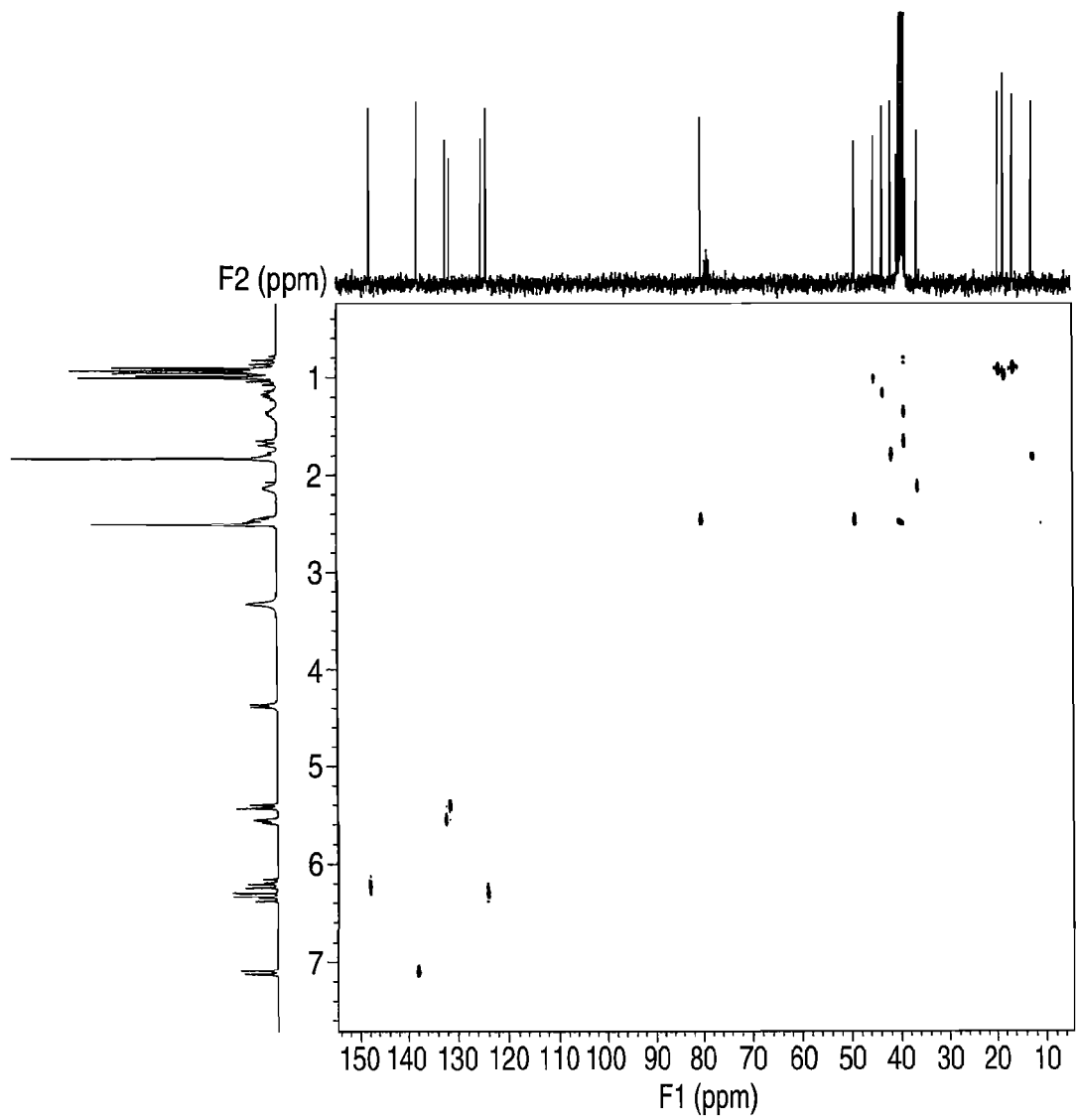
FIG. 1 represents the HMQC spectrum of (2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienoic acid (referred to as Compound A hereinafter), in which $^1H$ is expressed on the longitudinal axis and $^{13}C$ is expressed on the abscissa axis.

The compound of the invention is a product produced by the strain NFS-932 isolated from a litter layer in Ibaraki-city, Osaka-fu, Japan (Depository: International Patent Organism Depository, National Institute of Advanced Industrial Science and Technology; Deposition date: Nov. 15, 2004; Accession No.: FERM BP-10162) and a derivative thereof, as well as the pharmaceutically acceptable salts thereof.

Culturing the Strain NFS-932

The strain NFS-932 can be cultured by the conventional methods. For example, a small piece of NFS-932 grown in a potato-sucrose agar culture medium is planted in a sterile Erlenmeyer flask in which processed barley and distilled water are added, followed by static culture at 24° C. for one week as preculture. Then, the culture is added to a sterile petri dish in which processed barley and distilled water are added, as a seed. The resulting mixture is mixed together well, followed by static culture at 24° C. for 3 weeks for main culture, thereby complete the culturing.

Isolation of the Product Produced by the Bacterium

The product produced by the bacterium is isolated by the conventional methods. For example, methanol is added to the culture from culturing with processed barley, for pulverization with a homogenizer and extraction, followed by filtration under aspiration. An equal volume of water is added to the filtrate, which is then subjected to adsorption column chromatography. The adsorbed matter is eluted with methanol/water, and an active fraction is dried and solidified under reduced pressure. The residue is dissolved in a small amount of chloroform, subjected to silica gel chromatography, and eluted with chloroform/methanol. An active fraction is evaporated under reduced pressure. The residue is again subjected to silica gel column chromatography and is eluted with hexane/ethyl acetate. An active fraction is evaporated under reduced pressure. The residue is purified by high performance liquid chromatography. An isolated fraction is allowed to stand alone as it is, in order to deposit the crystal, followed by filtration and drying, thereby obtaining the product produced by the bacterium as colorless crystal.

Physicochemical Properties of the Product Produced by the Bacterium

Appearance: colorless crystal

Melting point: 216.0° C. to 218.6° C.

Solubility: soluble in methanol, chloroform and acetone but insoluble in water and hexane $R_f$ value (TLC aluminium sheet, silica gel $60F_{254}$, manufactured by Merck & Co., Inc.):

Toluene-ethyl acetate-90% formic acid (5:4:1) 0.66

Chlorform-acetone-2-propanol (85:15:20) 0.72

Molecular formula: $C_{19}H_{28}O_3$

Elemental Analysis value (as $C_{19}H_{28}O_3$)

Calculated (%): C, 74.96; H, 9.27.

Found (%): C, 74.79; H, 9.27.

EI-MS (M+): m/z 304

Rotation: $[\alpha]_D^{20}$ +58.71° (c 0.998, $CH_3OH$)

IR (KBr): ν 1667 $cm^{-1}$

Plane Structure of the Product Produced by the Bacterium

The molecular formula of the product produced by the bacterium was determined as $C_{19}H_{28}O_3O$, by EI-MS (m/z 304, M+) and the elemental analysis (calcd. for $C_{19}H_{28}O_3$: H, 9.27%; C, 74.96%. found: H, 9.27%; C, 74.79%). Further, the molecular formula was definitely certified by $^{13}C$ NMR and the DEPT spectrum (DMSO-$d_6$). Specifically, it was revealed that the product produced by the bacterium was composed of 4 methyl groups, one methylene group, 12 methine groups (7 aliphatic methines and 5 olefinic methines), one quaternary olefin carbon (δ 125.03 ppm) and one carboxyl carbon (δ 169.24 ppm; ν 1667 $cm^{-1}$). Additionally, 19 $^{13}C$ NMR signals were observed in total. The number was the same number as in the molecular formula (see Table 1).

Then, the plane structure was determined as follows, on the basis of the data from various NMR spectra (DMSO-$d_6$). First, all $^1H$ signals were assigned by the $^1H$-$^1H$ COSY spectrum (see Table 1). Characteristic signals were observed, which were 4 methyl doublets (one of them was from remote coupling), and 4 olefin double double doublets and one olefin double doublet (3 double bonds in total, taking account of the presence of one quaternary olefin carbon signal by $^{13}C$ NMR). Further, it was assumed that signals at δ 4.38 ppm and δ 12.13 ppm would indicate the bonding to oxygen atom, because no corresponding peak to $^{13}C$ was observed on the HMQC spectrum (see FIG. 1). Since the signal at δ 4.38 ppm indicates doublet, among them, secondary hydroxyl group is suggested, while the other signals at δ 12.13 ppm indicate carboxyl group due to the chemical shift. The unsaturated degree is 6 as indicated by the molecular formula ($C_{19}H_{28}O_3$). Since the presence of 3 double bonds and one carbonyl is suggested, the molecule might possibly be a bicyclic compound.

Figure 2:
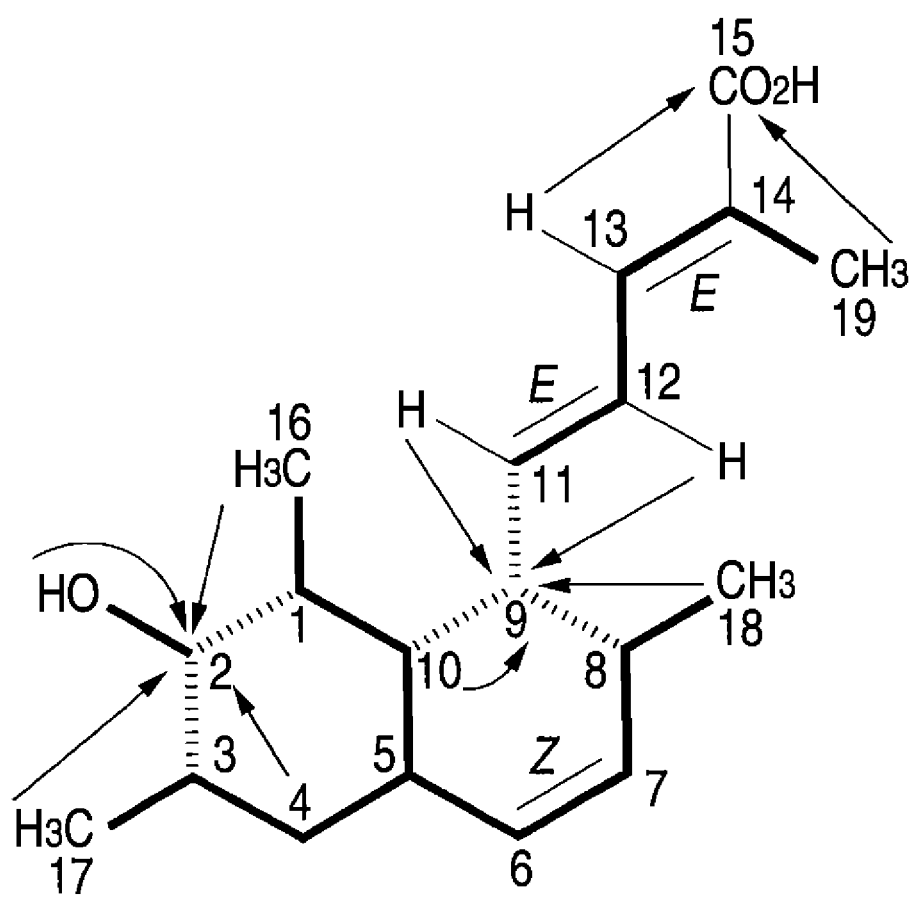
FIG. 2 schematically shows the plane structure of Compound A and the NMR correlation signals, in which the solid line and dotted line express the parts in the plane structure as determined by $^1H$-$^1H$ COSY, and the allows means the parts recognized to be correlated by HMBC spectrum.

Table 1 shows the $^1H$ and $^{13}C$ NMR chemical shifts (DMSO-$d_6$) of the product produced by the bacterium. Herein, the "Position" in the table expresses the carbon number on the plane structure in FIG. 2.

TABLE 1

$^1H$ and $^{13}C$ NMR chemical shifts (DMSO-$d_6$) of the product produced by the bacterium

| Position | δC (ppm) | Type | δH (ppm) [mult, J(Hz)] |
|---|---|---|---|
| 1 | 43.32 | CH | 1.17[1H, m] |
| 2 | 80.23 | CH | 2.46[1H, m] |
| 3 | 39.23 | CH | 1.37[1H, m] |
| 4 | 39.11 | $CH_2$ | 0.84[1H, q, 12.3] |
|  |  |  | 1.67[1H, dt, 13.2/3.3] |
| 5 | 41.63 | CH | 1.79[1H, m] |
| 6 | 131.38 | CH | 5.41[1H, dd, 11.1/1.8] |
| 7 | 132.25 | CH | 5.56[1H, ddd, 9.6/4.5/2.7] |
| 8 | 36.31 | CH | 2.11[1H, m] |
| 9 | 49.10 | CH | 2.46[1H, m] |
| 10 | 45.11 | CH | 1.02[1H, q, 9.9] |
| 11 | 147.96 | CH | 6.20[1H, dd, 15.3/10.5] |
| 12 | 124.07 | CH | 6.33[1H, dd, 15.0/11.1] |
| 13 | 137.92 | CH | 7.11[1H, dd, 11.1/1.5] |
| 14 | 125.03 | C |  |
| 15 | 169.24 | CO |  |
| 16 | 18.14 | $CH_3$ | 0.99[3H, d, 6.6] |
| 17 | 19.33 | $CH_3$ | 0.94[3H, d, 6.3] |
| 18 | 16.22 | $CH_3$ | 0.91[3H, d, 7.2] |
| 19 | 12.48 | $CH_3$ | 1.83[3H, d, 1.2] |
| 2-OH |  |  | 4.38[1H, d, 7.2] |
| COOH |  |  | 12.13[1H, br] |

Figure 3:
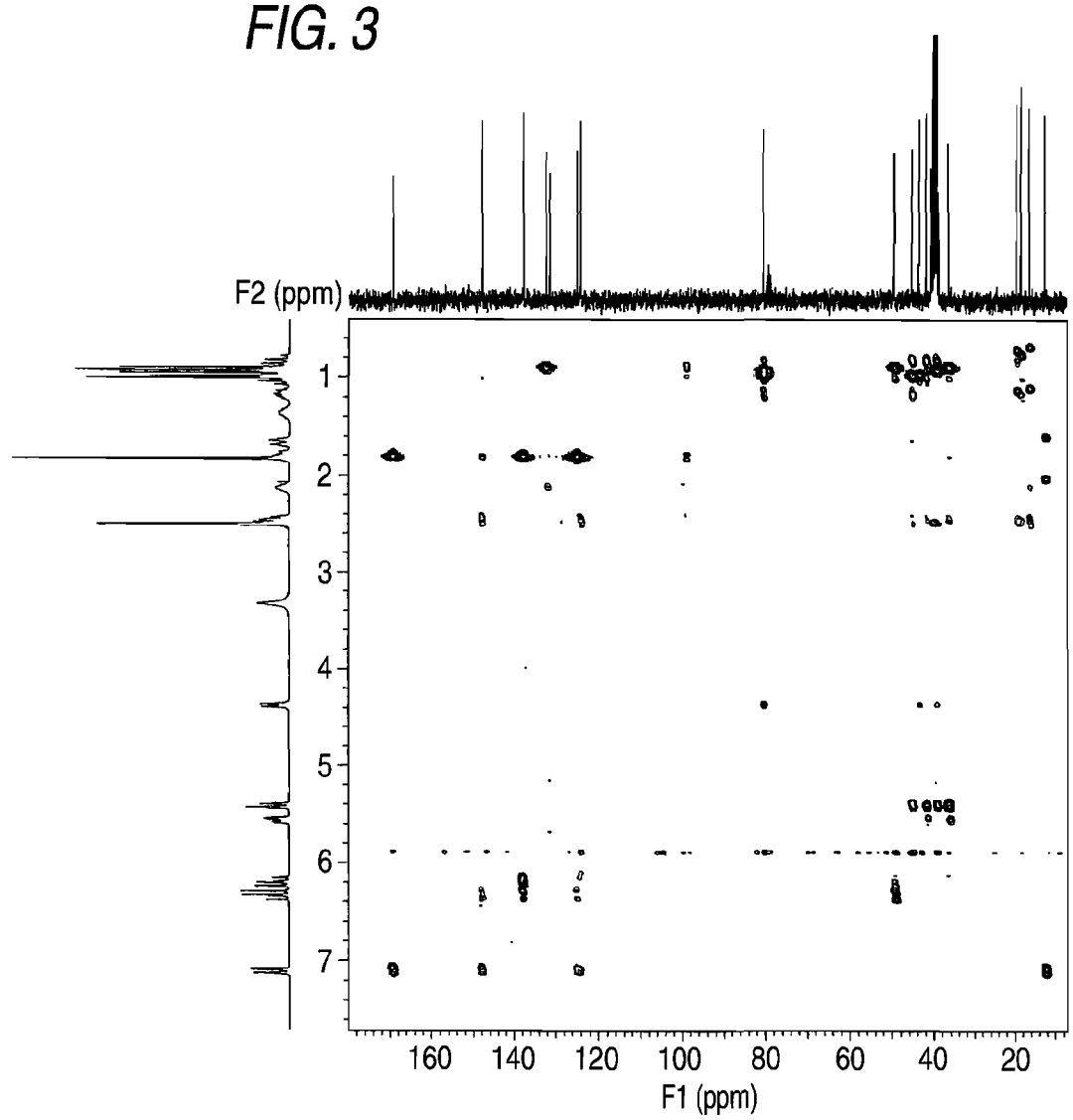
FIG. 3 represents the HMBC spectrum of Compound A, in which $^1H$ is expressed on the longitudinal axis and $^{13}C$ is expressed on the abscissa axis.

Using then the $^1H$-$^1H$ COSY and HMQC spectra, it was shown how the individual atoms were found together. The presence of three independent spin systems was revealed (see the broad line in FIG. 2). Continuously, H-2 and H-9 with unclear relations due to the overlap on the solvent signals were determined of their correlations, using the HMBC spectrum (see FIG. 3) (see the arrow in FIG. 2). Concerning the proton (H-2) with a correlation with hydroxyl proton (δ 4.38 ppm), first, correlation signals from 2-OH, H-4, H-16 and H-17 were observed toward the carbon (C-2, δ 80.23 ppm) bound with the proton. Accordingly, the proton was concluded as H-2. Concerning the remaining proton (H-9), additionally, correlation signals from H-10, H-11, H-12 and H-18 were observed toward the carbon (C-9, δ 49.10 ppm) bound with the proton. Accordingly, the proton was concluded as H-9. Once both the signals H-2 and H-9 could be discriminated as described above, these signals could be correlated appropriately (see the dotted line in FIG. 2). As to the position of the remaining carboxyl group, it was concluded that the carboxyl group bound to C-14 because of correlations with H-13 and H-19 toward the carbonyl carbon (C-15).

Figure 4:
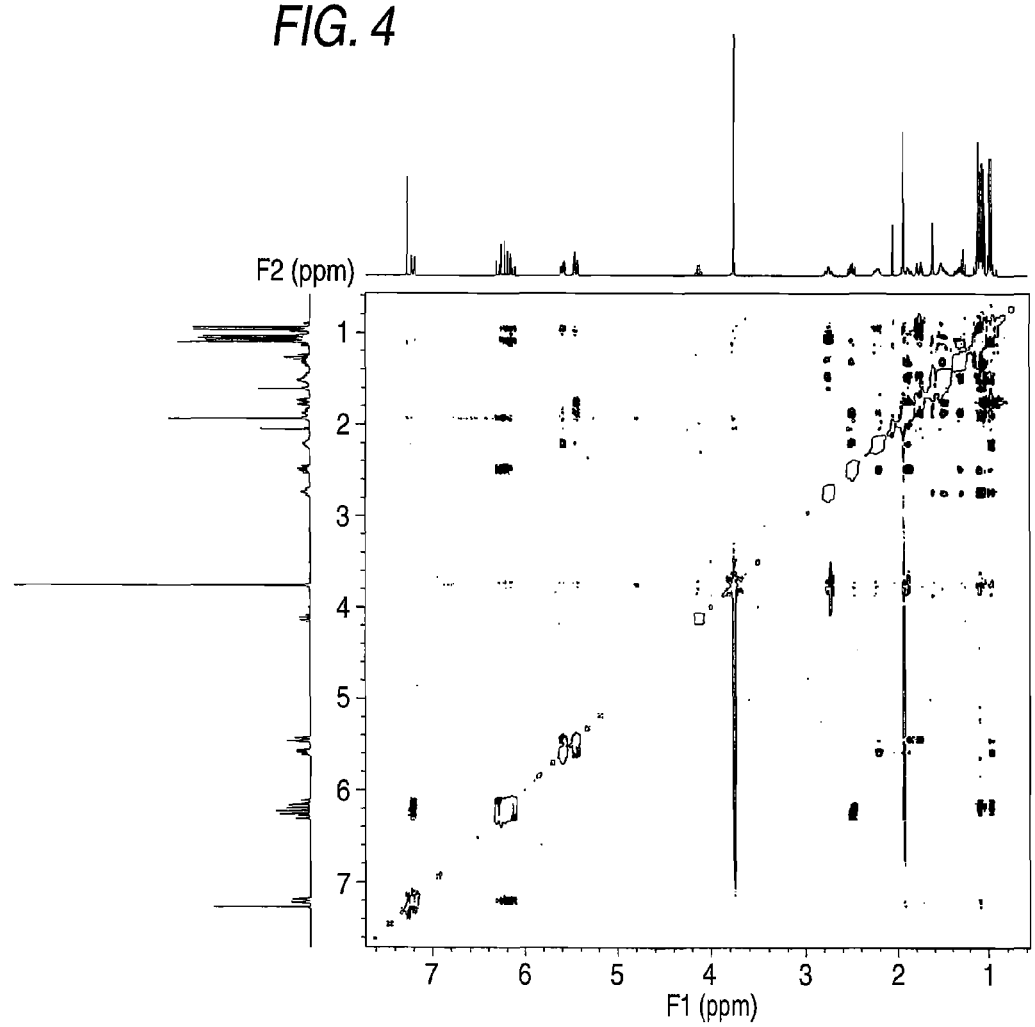
FIG. 4 represents the NOESY spectrum of the ester, in which $^1H$ is expressed on both the longitudinal axis and the abscissa axis.

Geometric isomerism of double bond was deduced on the basis of the coupling constants of corresponding olefin protons. As to the olefin in the ring, first, the coupling constant between H-6/H-7 is J=11.1 Hz. Thus, it was determined that these protons were in cis (Z configuration) to each other. Further, concerning the double bond (C-11/C-12) closer to the condensed ring among the two double bonds in the side chain, the coupling constant between H-11/H-12 was J=15.3 Hz. Accordingly, these protons were concluded as in trans (E configuration) to each other. Because one of the carbons in the remaining double bond (C-13/C-14) on the end in the side chain is quaternary carbon, the configuration cannot be determined on the basis of the coupling constant of olefin proton. Therefore, it was determined to make a judgment from the chemical shift of the $^{13}C$ NMR signal of the methyl group (C-19) bound to the tri-substituted olefin. Because the value is shifted as much as δ12.48 ppm toward a high magnetic field, specifically, it was determined that the methyl group and the olefin proton (H-13) were in the trans (namely, E configuration) relation to each other. The results are supported by the NOESY spectrum of methyl ester derivative (see FIG. 4).

As shown in FIG. 1, the plane structural formula of the product produced by the bacterium was determined on the basis of the physicochemical properties and the NMR structural analysis as described above. Thus, the product produced by the bacterium is (2E,4E)-5-(7-hydroxy-2,6,8-trimethyl-1,2,4a,5,6,7,8,8a-octahydronaphthalen-1-yl)-2-methylpenta-2,4-dienoic acid.

The Relative Steric Structure of the Product Produced by the Bacterium

In determining the relative steric structure of the product produced by the bacterium, the terminal carboxylic acid in the side chain of the product was once modified into methyl ester, because of many overlaps of the signals on $^1$H NMR spectra and because it was very hard to read the coupling constants near the solvent (DMSO-$d_6$) signal. The methyl ester (referred to as the ester herein) can be produced by the conventional methods, which has the following chemical values.

Elemental Analysis value (as $C_{20}H_{30}O_3$)
Calculated (%): C, 75.43; H, 9.50.
Found (%): C, 75.10; H, 9.44.
Rotation: $[\alpha]_D^{20}$ +71.64° (c 0.469, $CH_3OH$)
IR(KBr): ν 1709 $cm^{-1}$
$^1$H-NMR(CDCl$_3$) δ: 0.95[3H, d, 7.0(H-18)], 0.96[1H, q, 11.8(H-4$_{ax}$)], 1.04[3H, d, 6.2(H-16)], 1.08[3H, d, 6.4(H-17)], 1.08[1H, q, 9.7(H-10)], 1.32[1H, m(H-1)], 1.52[1H, m(H-3)], 1.75[1H, dt, 12.8/3.4(H-4$_{eq}$)], 1.85[1H, m(H-5)], 1.93[3H, d, 1.4(H-19)], 2.20[1H, m(H-8)], 2.49[1H, td, 9.4/5.6(H-9)], 2.74[1H, t, 8.8(H-2)], 3.75[3H, s(—CO$_2$CH$_3$)], 5.44[1H, dt, 9.4/1.8(H-6)], 5.59[1H, ddd, 9.6/4.0/2.6(H-7)], 6.14[1H, dd, 14.8/9.6(H-11)], 6.27[1H, dd, 15.0/10.6(H-12)], 7.20[1H, dq, 10.6/1.4(H-13)]

Figure 5:
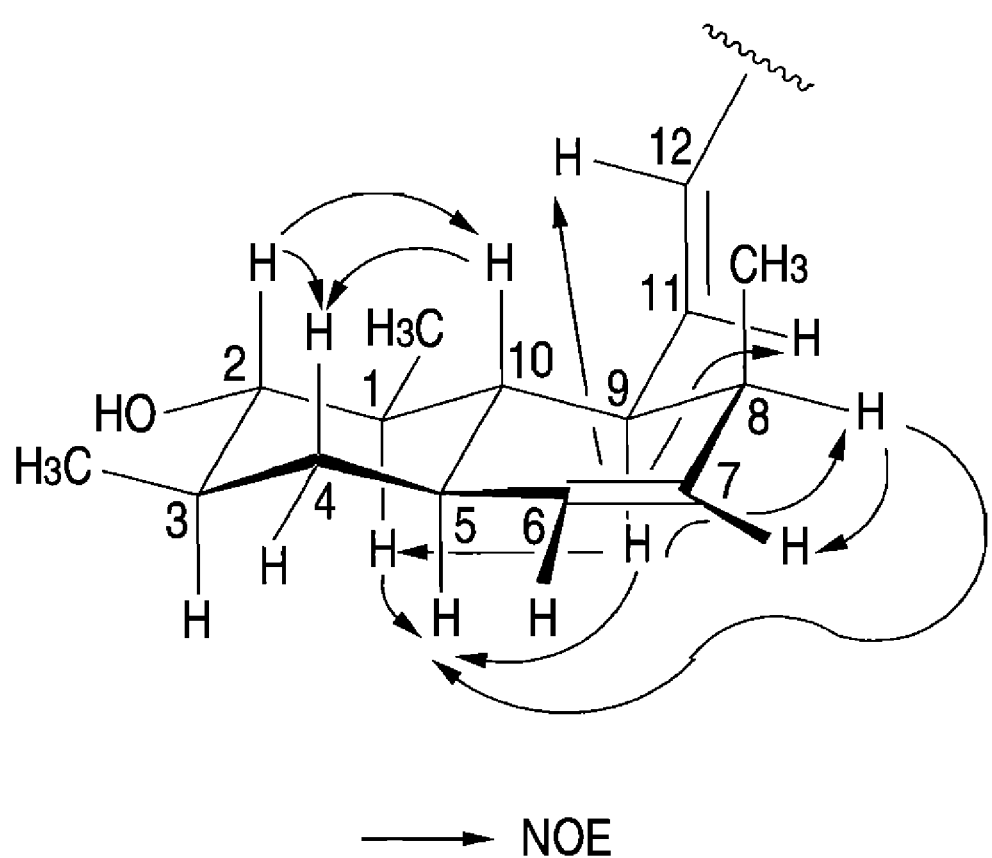
FIG. 5 represents the relative steric structure of the octahydronaphthalene-ring part in the ester and an NOE correlation, in which the arrow shows a part where NOE is observed.

The relative steric configuration of the part of the octahydronaphthalene ring in the ester was determined by using a combination of the vicinal coupling constants (see the chemical values described above) on the $^1$H NMR signal and the NOESY spectrum data (see FIG. 5). In conclusion, the H-2 methine proton (δ 2.74 ppm) is axially oriented because the proton is a triplet with a coupling constant of J=8.8 Hz, so the H-1 and H-3 adjacently located are essentially in axial orientation individually. In other words, the cyclohexane ring is in the chair type conformation, while the methyl groups at C-1 and C-3 positions and the hydroxyl group at the C-2 position are in equatorial orientation. On the other hand, NOEs were observed from H-2 toward the H-4 axial proton (H-4$_{ax}$, δ 0.96, q, J=11.8 Hz) and toward the H-10 (δ 1.08, q, J=9.7 Hz), while NOE was also observed between H-4 and H-10. Accordingly, these protons were concluded to be in a 1,3-diaxial relation to each other. Since both H-4 and H-10 are quartets with larger coupling constants, H-5 and H-6 adjacently located to them are also in the axial orientation. This is supported by the NOE observation between H-9 and H-1 or H-5. The similar NOE effect was observed between H-8 and H-9, but no NOE was observed between H-8 and H-10. Thus, it is concluded that H-8 is in the equatorial orientation. H-8 exerts NOE toward H-5 (weak) or H-7 (strong), but the former NOE can be explained by the flip of the pseudo-chair type/boat type conformation of the cyclohexane ring. Meanwhile, H-9 exerted NOE toward the olefin protons of H-11 and H-12 in the side chain.

Based on the above NMR structural analysis, the relative steric structure of the part of the octahydronaphthalene ring in the ester was determined as shown in FIG. 5.

Absolute Steric Structure of the Product Produced by the Bacterium

The absolute steric structure of the product produced by the bacterium was determined by applying the new Moscher method (Ohtani, I.; Kusumi, T.; Kashman, Y.; Kakisawa, H. J. Am. Chem. Soc. 1991, 113, 4092-4096) to the ester. The ester reacted with S- and R-MTPA chloride (α-methoxy-α-(trifluoromethyl)phenylacetyl chloride), to modify the ester individually into R- and S-MTPA esters, to determine the absolute steric structure due to the difference in chemical shift in the individual $^1$H NMR signals.

The chemical shift in the $^1$H NMR signal of the R-MTPA ester from the ester is shown below.

$^1$H-NMR(CDCl$_3$) δ: 0.80[3H, d, 6.2 (H-16)], 0.89[3H, d, 6.2(H-17)], 0.95[3H, d, 7.4(H-18)], 1.07[1H, q, 12.0(H-4$_{ax}$)], 1.16[1H, q, 10.0(H-10)], 1.59[1H, m(H-1)], 1.70[1H, m(H-3)], 1.81[1H, m(H-4$_{eq}$)], 1.87[1H, m(H-5)], 1.91[3H, d, 1.2(H-19)], 2.20[1H, m(H-8)], 2.47[1H, td, 9.4/5.6(H-9)], 3.55[3H, s(MTPA-OCH$_3$)], 3.75[3H, s(—CO$_2$CH$_3$)], 4.60[1H, t, 10.0(H-2)], 5.44[1H, dt, 9.6/1.4(H-6)], 5.61[1H, ddd, 9.2/4.0/2.6(H-7)], 6.09[1H, dd, 15.0/9.4(H-11)], 6.23[1H, dd, 15.0/10.2(H-12)], 7.16[1H, dd, 10.6/1.4(H-13)], 7.40[3H, m(MTPA-Ph)], 7.61[2H, m(MTPA-Ph)]

The chemical shift in the $^1$H NMR signal of the S-MTPA ester from the ester is shown below.

$^1$H-NMR(CDCl$_3$) δ: 0.80[3H, d, 6.4(H-17)], 0.89[3H, d, 6.2(H-16)], 0.96[3H, d, 7.0(H-18)], 1.05[1H, q, 12.0(H-4$_{ax}$)], 1.17[1H, q, 9.8(H-10)], 1.61[1H, m(H-1)], 1.68[1H, m(H-3)], 1.79[1H, m(H-4$_{eq}$)], 1.83[1H, m(H-5)], 1.93[3H, d, 1.0(H-19)], 2.22[1H, m(H-8)], 2.49[1H, td, 9.4/5.6(H-9)], 3.53[3H, s(MTPA-OCH$_3$)], 3.76[3H, s(—CO$_2$CH$_3$)], 4.61[1H, t, 10.0(H-2)], 5.44[1H, dt, 9.6/1.4(H-6)], 5.61[1H, ddd, 9.4/4.4/2.6(H-7)], 6.11[1H, dd, 15.0/9.8(H-11)], 6.25[1H, dd, 15.0/10.2(H-12)], 7.18[1H, dd, 10.4/1.4(H-13)], 7.40[3H, m(MTPA-Ph)], 7.61[2H, m(MTPA-Ph)]

Figure 6:
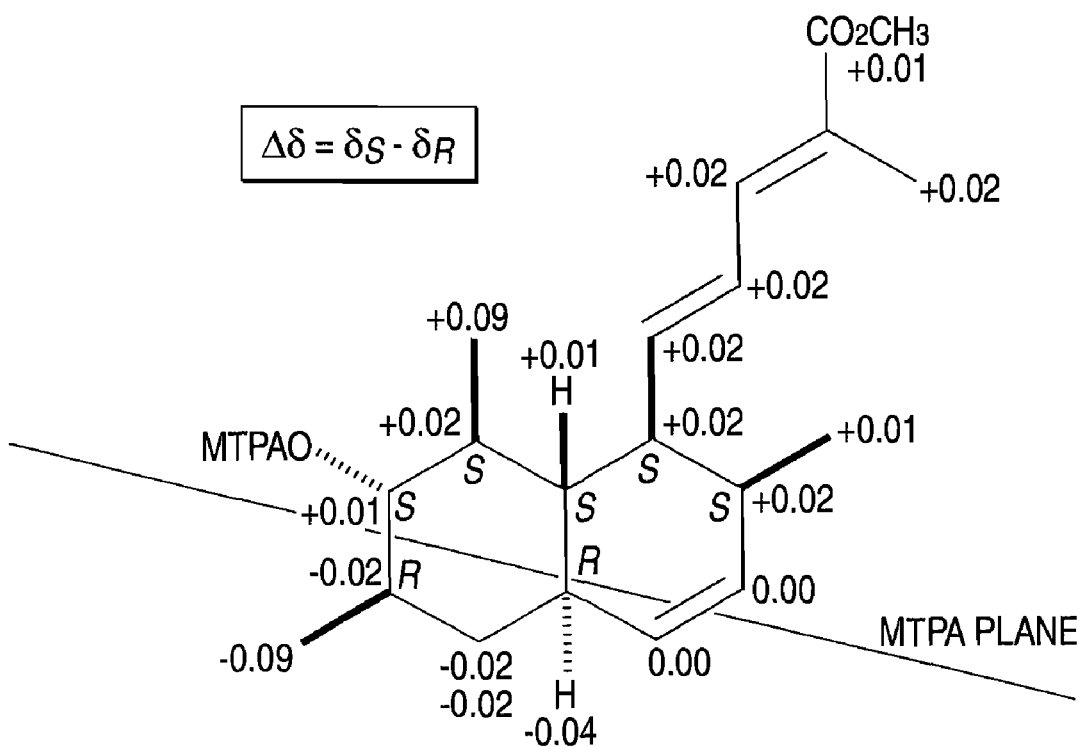
FIG. 6 represents the $\Delta\delta$ ($=\delta_S-\delta_R$) value of the MTPA ester in the ester and the absolute steric structure, in which the solid line expresses the MTPA plane.

Determining the difference in chemical shift ($\Delta\delta=\delta_S-\delta_R$) between the $^1$H NMR signals of both the MTPA esters, the value was plotted on the structural formula of the product produced by the bacterium (FIG. 6). Consequently, the positive values of $\Delta\delta$ are arranged on one side of the molecule (the upper part in FIG. 6) while the negative values thereof are arranged on the opposite side interfacing the MTPA plane (the lower part in FIG. 6). Based on the positive/negative signs and according to the rules of the new Moscher method, it was determined that the absolute stereochemistry of the carbon (C-2) bound with the secondary hydroxyl group MTPA-esterified was S. Thus, the remaining asymmetric carbons were sequentially determined from the C-2, according to the relative conformation previously revealed.

From the aforementioned results, it was determined that the absolute steric structure of the ester was determined as 1S, 2S, 3R, 5R, 8S, 9S, 10S, as shown in FIG. 6. Therefore, the product produced by the bacterium is (2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienoic acid (Compound A).

Derivative of the Product Produced by the Bacterium

The compound of the invention can be produced from the product produced by the bacterium and conventional compounds or readily preparable intermediates, for example by the following method. When a raw material contains a substituent having an influence on the reaction in producing the compound of the invention, generally, the raw material is preliminarily protected with an appropriate protective group by the conventional methods, for carrying out the reaction. The protective group can be eliminated after the reaction by the conventional methods.

The amide as a derivative of the product produced by the bacterium may readily be produced by the conventional method. For example, the amide may be produced by the following method.

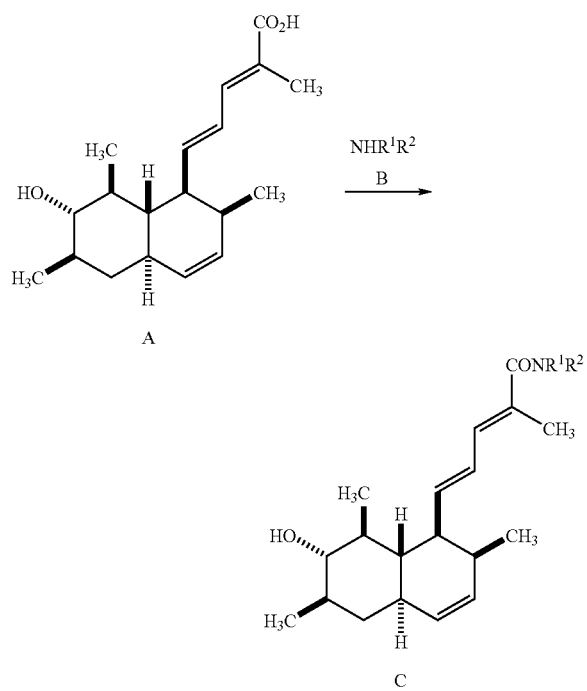

The reaction is a condensation reaction between Compound A as the product produced by the bacterium and Compound B. Therefore, the condensation can be carried out by the conventional methods. A carboxylic acid represented by Compound A or a reactive derivative thereof reacts with an amine represented by Compound B, to produce Compound C. The reactive derivative of Compound A includes those for general use in amide condensation, for example acid halide (for example, acid chloride, acid bromide), mixed acid anhydride, imidazolide, and active amide. In case of using Compound A, reaction is carried out in the presence or absence of a base (for example, organic amines such as triethylamine, N,N-diisopropyl-N-ethylamine, N,N-dimethylaniline, pyridine, 4-dimethylaminopyridine, 1,8-diazabicyclo[5.4.0]undec-7-ene), using a condensing agent (for example, 1,1'-oxalyldimidazole, 1-ethyl-3-(3-dimethylaminopropyl)carbodiimide, dicyclohexylcarbodiimide, diethyl cyanophosphonate, diphenylphosphorylazide, 2-chloro-1-methylpyridinium iodide, 1H-benzotriazol-1-yloxytripyrrolidinophosphonium hexafluorophosphate, benzotriazol-1-yloxytris(dimethylamino)phosphonium hexafluorophosphate) at −20° C. to 100° C. The solvent to be used includes but is not specifically limited to ethers such as tetrahydrofuran and diethyl ether, amides such as N,N-dimethylformamide and N,N-dimethylacetoamide, nitriles such as acetonitrile and propionitrile, hydrocarbons such as benzene and toluene, halogenated hydrocarbons such as chloroform and dichloromethane, or mix solvents thereof. Then, additives (1-hydroxybenzotriazole, N-hydroxysuccinimide and the like) may also be added. The reaction time varies depending on the types of the raw material and the condensing agent, the reaction temperature, and the like. However, the reaction time is appropriately 30 minutes to 24 hours. The amounts of the Compound B and the condensing agent used are preferably an amount one- to 3-fold that of the Compound A. In case of using for example an acid halide as a reactive derivative of the Compound A, pyridine-series solvents such as pyridine and 4-methylpyridine or the same bases along with the same solvents as described above are used, for reaction at −20° C. to 100° C. As such additive, for example, 4-dimethylaminopyridine may be added. The reaction time varies depending on the type of the acid halide used and the reaction temperature. Generally, the reaction time is appropriately 30 minutes to 24 hours.

An ester derivative of the product produced by the bacterium (for example, see Example 2), a hydroxymethyl derivative thereof (for example, see Example 3), and an alkoxymethyl derivative thereof (for example, see Example 4) can readily be produced by known methods.

The octahydronaphthalene derivative in accordance with the invention may be used as a pharmaceutical agent as it is. In case of forming a pharmaceutically acceptable salt thereof, however, such salt includes, for example, salts thereof with mineral acids such as hydrochloric acid, hydrobromic acid, sulfuric acid and phosphoric acid, salts thereof with organic acids such as acetic acid, citric acid, tartaric acid, maleic acid, succinic acid, fumaric acid, p-toluenesulfonic acid, benzenesulfonic acid, and methanesulfonic acid, salts thereof with inorganic bases such as sodium, potassium, calcium, magnesium and ammonium, salts thereof with organic bases such as methylamine, diethylamine, triethylamine, triethanolamine, ethylenediamine, tris(hydroxymethyl)methylamine, guanidine, choline, and cinchonine, and salts thereof with amino acids such as lysine, arginine and alanine.

The hydrochloride salt of an octahydronaphthalene derivative in accordance with the invention can be obtained, for example, by dissolving the octahydronaphthalene derivative in accordance with the invention in an alcohol solution of hydrogen chloride, an ethyl acetate solution thereof or an ether solution thereof.

Furthermore, hydrous products, hydrated products and solvated products of the individual compounds are also encompassed within the scope of the invention.

When the compound of the invention is to be administered as a pharmaceutical drug, the compound of the invention can be administered as it is or can be administered as a pharmaceutical composition in a non-toxic and inactive carrier pharmaceutically acceptable, at a content of, for example, 0.1% to 99.5%, preferably 0.5% to 90%, to mammals including humans.

As the carrier, one or more types of diluents, fillers and other auxiliary agents for formulation, in solids, semi-solids and liquids, are used. The pharmaceutical composition is preferably administered in a unit dose. The pharmaceutical composition in accordance with the invention may be administered intravenously, orally, by dosing into tissues, topically (by for example transdermal dosing), or trans-rectally. It is needless to say that the pharmaceutical composition is administered in a dosage form suitable for such dosing methods.

The dose as an agent for suppressing ICAM-1 expression, a therapeutic agent for inflammatory diseases or an agent for suppressing cell growth is preferably determined, taking account of the nature and severity of a disease, the state of a patient, such as age and body weight, and the administration route. Generally, the amount of the active ingredient as the compound of the invention per adult is within a range of 0.1 to 1000 mg/individual human daily, preferably 1 to 500 mg/individual human daily.

In some case, a dose below the range is satisfactory or a dose above the range may be needed. Additionally, the dose may be given in two or three dividend portions.

EXAMPLES

The invention is now described further in detail in the following Reference Examples, Examples, Test Examples and Formulation Examples. However, the invention is not limited thereto.

Reference Example 1

Synthetic Preparation of R-MTPA Ester as the Ester

In 1 ml of pyridine, 32 mg of the compound obtained in Example 2 was dissolved, to which 51 mg of (S)-(+)-α-methoxy-α-(trifluoromethyl)phenylacetyl chloride ((S)-(+)-MTPA chloride) was added dropwise under stirring at ambient temperature. After stirring at ambient temperature for 14 hours, saturated aqueous sodium hydrogen carbonate solution was added to the reaction solution, followed by extraction with ethyl acetate. After washing with water, the extract was dried over anhydrous magnesium sulfate, from which the solvent was evaporated under reduced pressure. The residue was purified by silica gel column chromatography (Wako Gel C-200, manufactured by Wako Pure Chemical Industry Co., Ltd.; 3 g), to obtain the intended compound of 39 mg in colorless oily matter.

$^1$H-NMR(CDCl$_3$) δ: 0.80[3H,d], 0.89[3H,d], 0.95[3H,d], 1.07[1H,q], 1.16[1H,q], 1.59[1H,m], 1.70[1H,m], 1.81[1H,m], 1.87[1H,m], 1.91[3H,d], 2.20[1H,m], 2.47[1H,td], 3.55[3H,s], 3.75[3H,s], 4.60[1H,t], 5.44[1H,dt], 5.61[1H,ddd], 6.09[1H,dd], 6.23[1H,dd], 7.16[1H,dd], 7.40[3H,m], 7.61[2H,m]

Reference Example 2

Synthetic Preparation of S-MTPA Ester as the Ester

In 1 ml of pyridine, 32 mg of the compound obtained in Example 2 was dissolved, to which 51 mg of (R)-(−)-α-methoxy-α-(trifluoromethyl)phenylacetyl chloride ((R)-(−)-MTPA chloride) was added dropwise under stirring at ambient temperature. After stirring at ambient temperature for 14 hours, saturated aqueous sodium hydrogen carbonate solution was added to the reaction solution, followed by extraction with ethyl acetate. After washing with water, the extract was dried over anhydrous magnesium sulfate, from which the solvent was evaporated under reduced pressure. The residue was purified by silica gel column chromatography (Wako Gel C-200, manufactured by Wako Pure Chemical Industry, Co., Ltd.; 3 g), to obtain the intended compound of 32 mg in colorless oily matter.

$^1$H-NMR(CDCl$_3$) δ: 0.80[3H,d], 0.89[3H,d], 0.96[3H,d], 1.05[1H,q], 1.17[1H,q], 1.61[1H,m], 1.68[1H,m], 1.79[1H,m], 1.83[1H,m], 1.93[3H,d], 2.22[1H,m], 2.49[1H,td], 3.53[3H,s], 3.76[3H,s], 4.61[1H,t], 5.44[1H,dt], 5.61[1H,ddd], 6.11[1H,dd], 6.25[1H,d], 7.18[1H,dd], 7.40[3H,m], 7.61[2H,m]

Example 1

Compound A (1) Collection of Bacterium

The strain NFS-932 isolated from a litter layer in Ibaraki-city, Osaka-fu, Japan (Depository: International Patent Organism Depository, National Institute of Advanced Industrial Science and Technology; Deposition date: Nov. 15, 2004; Accession No.: FERM BP-10162) was used. Comparing the strain with previously reported bacteria in terms of spore formation, hyphae morphology, growth rate and color on various culture media, the bacterium was identified as one of incomplete bacteria belonging to the genus *Trichoderma*.

(2) Culturing the Strain NFS-932

A piece of NFS-932 as grown in a potato-sucrose agar culture medium was planted in a sterile Erlenmeyer flask in which 10 g of the processed barley "Hatsuratsu (manufactured by Hakubaku)" and 5 ml of distilled water are added, followed by static culture at 24° C. for one week as preculture. Then, the culture was added to a sterile petri dish in which 250 g of the processed barley and 125 ml of distilled water are added, as a seed. The resulting mixture was thoroughly mixed together, followed by static culture at 24° C. for 3 weeks as main culture.

(3) Isolation and Purification of Compound A

To 1 kg of the culture resulting from culturing with the processed barley, 3 liters of methanol were added. Then, pulverization with a homogenizer and extraction were carried out, followed by filtration under aspiration. An equal volume of water was added to the filtrate, which was then subjected to adsorption column chromatography (DIAION HP-20, manufactured by Mitsubishi Kasei; 250 ml). The adsorbed matter was eluted with 1 liter of each of 40, 60, 80, 100% methanol/water. Fractions eluted with 80% and 100% methanol/water were combined together, and evaporated under reduced pressure (3.46 g). The residue was dissolved in a small volume of chloroform, and was then applied to silica gel column chromatography (Wako gel C-200, manufactured by Wako Pure Chemical Co., Ltd.; 170 g). Raising the methanol concentration in chloroform in a step-wise manner for elution, fractions eluted with 1 to 2% methanol/chloroform were collected and dried under reduced pressure (0.54 g). The residue was again subjected to silica gel column chromatography (Wako gel C-200, manufactured by Wako Pure Chemical Co., Ltd.; 25 g). Raising the ethyl acetate concentration in hexane in a step-wise manner, elution was carried out. A part of the active fraction was dried under reduced pressure (0.07 g). The residue was purified by HPLC (Capsule pack C$_{18}$ UG80, 250 mm×20 mm I.D., manufactured by Shiseido Co., Ltd.). The isolated fraction was allowed to stand alone as it was, to deposit the crystal, which was filtered and dried, so that the intended compound was obtained in colorless crystal (0.03 g).

Appearance: colorless crystal

Melting point: 216.0° C. to 218.6° C.

Solubility: soluble in methanol, chloroform and acetone but insoluble in water and hexane R$_f$ value (TLC aluminium sheet, silica gel 60F$_{254}$, manufactured by Merck & Co., Inc.):

Toluene-ethyl acetate-90% formic acid (5:4:1) 0.66

Chlorform-acetone-2-propanol (85:15:20) 0.72

Molecular formula: C$_{19}$H$_{28}$O$_3$

Elemental Analysis value (as C$_{19}$H$_{28}$O$_3$)

Calculated (%): C, 74.96; H, 9.27.

Found (%): C, 74.79; H, 9.27.
EI-MS (M$^+$): m/z 304
Rotation: $[\alpha]_D^{20}$+58.71° (c 0.998, CH$_3$OH)
IR (KBr): ν 1667 cm$^{-1}$ Example 2

Methyl (2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienoate In 2 ml of tetrahydrofuran-methanol (4:1), 100 mg of Compound A was dissolved, to which 197 μl of trimethylsilyldiazomethane (2.0 M hexane solution) was added dropwise under stirring at ambient temperature. The resulting mixture was stirred at ambient temperature for 1.5 hours. After the solvent was evaporated under reduced pressure, the residue was purified by silica gel column chromatography (Wako gel C-200, manufactured by Wako Pure Chemical Co., Ltd.; 6 g), to obtain the intended compound at 105 mg in colorless crystal.

Melting point: 54° C. to 57° C.
Elemental Analysis value (as C$_{20}$H$_{30}$O$_3$)
Calculated (%): C, 75.43; H, 9.50.
Found (%): C, 75.10; H, 9.44.
Rotation: $[\alpha]_D^{20}$+71.64° (c 0.469, CH$_3$OH)
IR(KBr): ν 1709 cm$^{-1}$
$^1$H-NMR(CDCl$_3$) δ: 0.95[3H,d], 0.96[1H,q], 1.04[3H,d], 1.08[3H,d], 1.08[1H,q], 1.32[1H,m], 1.52[1H,m], 1.75[1H,dt], 1.85[1H,m], 1.93[3H,d], 2.20[1H,m], 2.49[1H,td], 2.74[1H,t], 3.75[3H,s], 5.44[1H,dt], 5.59[1H,ddd], 6.14[1H,dd], 6.27[1H,dd], 7.20[1H,dq]

Example 3

(2E,4E)-5-[(1S,2S,4aR,6R,7S,8S,8aS)-7-Hydroxy-2,6,8-trimethyl-1,2,4a,5,6,7,8,8a-octahydronaphthalen-1-yl]-2-methylpenta-2,4-dien-1-ol In 2 ml of tetrahydrofuran, 37 mg of lithium aluminium hydride was suspended. The inside of the system was substituted with argon. Under stirring at ambient temperature, 2 ml of a solution of 200 mg of Compound A in tetrahydrofuran was added dropwise over 10 minutes, for reflux under heating for 24 hours. After the reaction solution was cooled with ice, 0.37 ml of water, 0.37 ml of aqueous 15% sodium hydroxide solution and 1.11 ml of water were sequentially added dropwise. Then, the reaction system was taken out of the ice bath. Then, the reaction mixture was stirred at ambient temperature for 30 minutes until gray insoluble matters turned white. The insoluble matters were filtered off. The resulting filtrate was concentrated under reduced pressure. Saturated aqueous sodium hydrogen carbonate solution was added to the resulting residue, followed by extraction with ethyl acetate. After washing with water, the extract was dried over anhydrous magnesium sulfate, from which the solvent was evaporated under reduced pressure. The residue was purified by silica gel column chromatography (PSQ 100B, manufactured by Fuji Silicia; 20 g), to obtain the intended compound at 124 mg in colorless amorphous.

Elemental Analysis value (as C$_{19}$H$_{30}$O$_2$.0.7H$_2$O))
Calculated (%): C, 75.30; H, 10.44.
Found (%): C, 75.26; H, 9.94.
Rotation: $[\alpha]_D^{20}$+15.11° (c 0.900, CH$_3$OH)
$^1$H-NMR(DMSO-d$_6$) δ: 0.82[1H,q], 0.89[3H,d], 0.93[3H,d], 0.96[1H,m], 1.00[3H,d], 1.14[1H,m], 1.34[1H,m], 1.65[1H,dt], 1.65[3H,s], 1.78[1H,m], 2.08[1H,m], 2.33[1H,dd], 2.43[1H,dd], 3.83[2H,d], 4.36[1H,d], 4.76[1H,t], 5.39[1H,d], 5.55[1H,ddd], 5.67[1H,dd], 5.99[1H,dd], 6.18[1H,dd]

Example 4

(2E,4E)-5-[(1S,2S,4aR,6R,7S,8S,8aS)-7-Hydroxy-2,6,8-trimethyl-1,2,4a,5,6,7,8,8a-octahydronaphthalen-1-yl]-2-methylpenta-2,4-dienyl-methyl ether In 2 ml of tetrahydrofuran, 85 mg of the compound obtained in Example 3 was dissolved, to which 22 μl of methyl iodide and 29 mg of 60% sodium hydride were sequentially added, for stirring at ambient temperature for 24 hours. Water was added to the resulting reaction solution, followed by extraction with ethyl acetate. The extract was dried over anhydrous magnesium sulfate, from which the solvent was evaporated under reduced pressure. The residue was purified by silica gel column chromatography (PSQ 100B, manufactured by Fuji Silicia; 10 g), to obtain the intended compound at 62 mg in colorless oily matter.

Elemental Analysis value (as C$_{20}$H$_{32}$O$_2$.0.1H$_2$O)
Calculated (%): C, 78.43; H, 10.60.
Found (%): C, 78.21; H, 10.61.
Rotation: $[\alpha]_D^{20}$+10.94° (c 0.457, CH$_3$OH) $^1$H-NMR (CDCl$_3$) δ: 0.94[1H,q], 0.94[3H,d], 1.04[3H,d], 1.10[3H,d], 1.27[1H,m], 1.36[1H,m], 1.50[1H,m], 1.75[1H,dt], 1.75[3H,d], 1.86[1H,m], 2.17[1H,m], 2.41[1H,ddd], 2.73[1H,t], 3.31[3H,s], 3.85[2H,s], 5.42[1H,dt], 5.59[1H,ddd], 5.74[1H,dd], 6.02[1H,dq], 6.17[1H,dd]

Example 5

N-(Pyridin-3-ylmethyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide In 45 ml of N,N-dimethylformamide, 3.04 g of Compound A was dissolved, to which 2.11 g of 1-ethyl-3-(3-dimethylaminopropyl)carbodiimide hydrochloride and 1.84 g of 1-hydroxybenzotriazole were added, followed by stirring at ambient temperature for 30 minutes. Under stirring at ambient temperature, 5 ml of a solution of 1.19 g of 3-(aminomethyl)pyridine in N,N-dimethylformamide and 3 ml of triethylamine were sequentially added. After stirring at ambient temperature for 18 hours, water was added to the reaction solution, followed by extraction with ethyl acetate. The extract was washed with water and dried over anhydrous magnesium sulfate, from which the solvent was evaporated under reduced pressure. The crude crystal obtained was rinsed with ethyl acetate, to obtain the intended compound at 2.85 g in colorless crystal.

Melting point: 163° C. to 164° C.
Elemental Analysis value (as C$_{25}$H$_{34}$N$_2$O$_2$)
Calculated (%): C, 76.10; H, 8.69; N, 7.10.
Found (%): C, 75.84; H, 8.67; N, 7.02.
Rotation: $[\alpha]_D^{20}$+76.69° (c 1.103, CH$_3$OH)
IR(KBr): ν 1653 cm$^{-1}$
$^1$H-NMR(DMSO-d$_6$) δ: 0.84[1H,q], 0.91[3H,d], 0.94[3H,d], 1.01[3H,d], 1.02[1H,q], 1.18[1H,m], 1.37[1H,m], 1.67[1H,dt], 1.80[1H,t], 1.89[3H,s], 2.12[1H,m], 2.44[1H,m], 2.46[1H,m], 4.35[2H,d], 4.38[1H,d], 5.42[1H,dd], 5.56[1H,ddd], 6.05[1H,dd], 6.31[1H,dd], 6.87[1H,d], 7.33[1H,dd], 7.66[1H,dt], 8.41[1H,d], 8.44[1H,dd], 8.49[1H,d]

The following compounds were synthesized in the same manner as Example 5.

Example 6

N-(Pyridin-4-ylmethyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 7

N-(Pyridin-2-ylmethyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 8

N-Benzyl-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 9

N-(3-Methoxybenzyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 10

N-(4-Chlorobenzyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 11

N-(4-Methylbenzyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 12

N-[4-(N',N'-Dimethylamino)benzyl]-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 13

N-(Pyridin-4-ylethyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 14

N-(4-Hydroxyphenethyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 15

N-(Phenylbutyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 16

N-Phenyl-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 17

N-Methyl-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 18

N-(n-Butyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 19

N-(t-Butyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 20

N,N-Dimethyl-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 21

N-Benzyl-N-methyl-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide

Example 22

(2E,4E)-5-[(1S,2S,4aR,6R,7S,8S,8aS)-7-Hydroxy-2,6,8-trimethyl-1,2,4a,5,6,7,8,8a-octahydronaphthalen-1-yl]-2-methylpenta-2,4-dienamide

Test Example 1

Test about Suppression of ICAM-1 Expression (Enzyme Immuno Assay, EIA)

Using a culture broth containing serum for vascular endothelial cell (manufactured by Nissui Pharmaceutical Co., Ltd.) as a culture medium, HUVEC (umbilical vein endothelial cell manufactured by Morinaga Bioscience Institute) was cultured in a collagen-treated flask by the routine method.

For carrying out a test about the suppression of ICAM-1 expression with HUVEC, a collagen-treated 96-well plate was used, where HUVEC was added at 1 to $2 \times 10^4$ cells/well while the culture medium was added at 100 to 200 µl/well. The cell was cultured in 5% $CO_2$ at 37° C. for 48 to 72 hours.

Before adding a test solution, the culture medium (80 μl) was exchanged, to which 10 μl of a test solution preliminarily diluted was then added. The plate was allowed to stand alone in a $CO_2$ incubator. 2 hours later, 10 μl of TNF-α (recombinant human TNF-α, manufactured by Genzyme) was added (to a final concentration of 0.3 ng/ml). The resulting plate was again allowed to stand alone in the $CO_2$ incubator. 16 to 22 hours later, the cell was fixed with 1% p-formaldehyde solution. The cell was rinsed with a phosphate buffer containing $Ca^{2+}$ and $Mg^{2+}$, which was then treated with an anti-human ICAM-1 antibody (mouse IgG1, manufactured by Kyowa Medics) at ambient temperature for 30 minutes. After the cell was rinsed again with the phosphate buffer, the cell was treated with a peroxide-labeled anti-mouse IgG (H+L) (manufactured by Organon Teknik Corp.) for another 30 minutes. After the cell was again rinsed with the phosphate buffer, the color developed was measured, using a peroxidase chromogenic kit (manufactured by Sumitomo Bakelite Co., Ltd.), to determine ICAM-1 expressed on HUVEC as an expression-inhibiting ratio (%) to a non-drug group to calculate the $IC_{50}$ value. The results are shown in Table 2.

TABLE 2

Test for suppressing ICAM-1 expression

| Test drug | $IC_{50}$ (×10 μM) |
| --- | --- |
| Example 1 | 5.9 |
| Example 2 | 0.067 |
| Example 3 | 0.99 |
| Example 4 | 0.22 |
| Example 5 | 0.017 |
| Example 6 | 0.059 |
| Example 7 | 0.20 |
| Example 8 | 0.047 |
| Example 9 | 0.21 |
| Example 10 | 14 |
| Example 11 | 16 |
| Example 12 | 32 |
| Example 13 | 0.57 |
| Example 14 | 1.5 |
| Example 16 | 1.5 |
| Example 17 | 0.26 |
| Example 18 | 0.24 |
| Example 19 | 1.5 |
| Example 20 | 0.14 |
| Example 21 | 0.49 |
| Example 22 | 0.88 |

As shown in Table 2, apparently, the compound of the invention has an activity of suppressing ICAM-1 expression.

Test Example 2

Methylated Human Serum Albumin-Induced Delayed Hypersensitivity Test (MeHSA-DTH)

Methylated human serum albumin (MeHSA) was dissolved in physiological saline to 5 mg/ml, which was then mixed with an equal volume of the complete Freund's adjuvant (manufactured by Iatron), to prepare an emulsion. Next, 100 μl of the prepared emulsion was injected subcutaneously into a 8-week-old male C57BL/6 mouse, for antigen sensitization. Seven days thereafter, MeHSA was dissolved in physiological saline to 1 mg/ml, which was injected at 25 μl subcutaneously into the footpad of the right hind limb, to trigger a reaction. The thickness of the footpad was measured 24 hours after the induction of the reaction, to calculate the difference from the thickness thereof before the induction of the reaction, to make an assessment. Additionally, drugs were orally given twice, namely one hour before the induction of the reaction and 16 hours after the induction thereof. The results are shown in Table 3.

TABLE 3

Methylated human serum albumin-induced delayed hypersensitivity test

| Test drug | Dose (mg/kg) | Suppression ratio (%) |
| --- | --- | --- |
| Example 5 | 10 | 27.5* |
|  | 30 | 51.5** |
| Example 6 | 10 | 27.8* |
|  | 30 | 35.7** |

*P < 0.01
**P < 0.05 (Dunnet's test)

As shown in Table 3, apparently, the compound of the invention is useful for therapeutic treatment of inflammatory diseases due to the invasion of lymphocyte.

Test Example 3

Test Using Collagen Arthritis Model in Mouse

Type II collagen derived from bovine joint was dissolved in 0.1 M acetate saline to 2 mg/ml, with which an equal volume of the complete Freund's adjuvant (manufactured by Iatron) was mixed, to prepare an emulsion. For primary sensitization, the emulsion was injected intracutaneously into the tail root of a 8-week-old male DBA/1J mouse. Twenty-one days thereafter, 0.1 ml of an emulsion prepared in the same manner was intracutaneously injected into the dorsal part of the mouse, for secondary sensitization, to trigger the onset of arthritis. Two weeks after the secondary sensitization, the symptoms of arthritis were visually observed (0: normal; 1: swelling and reddening of finger tips; 2: mild swelling and reddening of parts distal from joints of hands and foots; 3: severe swelling and reddening of parts distal from joints of hands and foots). The symptoms of arthritis were observed individually over the four limbs. The total was defined as the arthritis score of an individual. Further, a test drugs was suspended in 0.5% methyl cellulose and orally given daily after the secondary sensitization. The results are shown in Table 4.

TABLE 4

Test using collagen-induced arthritis model in mouse

| Test drug | Dose (mg/kg) | Case number | Arthritis score |
| --- | --- | --- | --- |
| Non-drug group | — | 10 | 5.7 |
| Example 5 | 30 | 9 | 2.1* |

*P < 0.05 (Wilcoxon's rank sum test)

As shown in Table 4, apparently, the compound of the invention is useful for therapeutic treatment of rheumatoid arthritis.

Subsequently, examination was carried out as to whether or not the compound of the invention had an action of suppressing cell growth.

Test Example 4

Test about the Suppression of Cell Growth

Various cancer cells and normal cell as cultured in a culture broth to 70 to 90% confluency were used. After the culture broth was removed, 0.25% trypsin/1 mM-EDTA solution was added to scrape off the cells and count the cells. Then, a cell suspension of 5×10⁴ cells/ml was prepared. The suspension was divided at 90 μl/well into a 96-well plate, and allowed to stand alone in a $CO_2$ incubator. On the next day, (a 0 to 10 μM test drug (the compound of Example 5) was added at 10 μl/well, for gentle shaking for sufficiently mixing the test drug with the liquid culture. After culturing for 3 days, each 10-μl portion of aqueous 5 mg/ml MTT (3-(4,5-dimethylthiazol-2-yl)-2,5-diphenyltetrazolium bromide) solution was added. After culturing in the $CO_2$ incubator for another 4 hours, 100 μl of a 2-propanol solution containing 0.04N hydrochloric acid was added to each well, for terminating the reaction. The generated MTT formazan was sufficiently dissolved with a multi-channel pipette, to measure the absorbance at 595 nm, using a control wavelength of 655 nm. The measured absorbance was analyzed by non-linear regression analysis using a model formula by the MTT method, to calculate the concentration at which the cell growth was inhibited by 50% ($IC_{50}$). The cells used at this test and the culture broths therefor are as shown below.

1) Cell: A549 (human lung cancer cell, Human Science Foundation)
   Culture broth: DMEM (Dulbecco's modified Eagle medium)+10% FBS (fetal bovine serum)
2) Cell: PC-3 (human prostate cancer cell, ATCC)
   Culture broth: DMEM+10% FBS
3) Cell: AsPC-1 (human pancreas cancer cell, Tokyo University)
   Culture broth: DMEM+10% FBS
4) Cell: HT-1080 (human fibrosarcoma cell, ATCC)
   Culture broth: DMEM+10% FBS
5) Cell: Hepatocyte (normal human liver cell, ACRBI)
   Culture broth: CS-C (Cell Systems)
6) Cell: NHDF (normal human fibroblast cell, Kurabo)
   Culture broth: DMEM+10% FBS
7) Cell: BAE (normal bovine aorta vascular endothelial cell, ACRBI)
   Culture broth: CS-C (Cell systems)

The results of the test are shown in Table 5.

TABLE 5

Test about the suppression of cell growth

| Cell | $IC_{50}$ (nM) |
|---|---|
| A549 (human lung cancer) | 85 |
| PC-3 (human prostate cancer) | 67 |
| AsPC-1 (human pancreas cancer) | 113 |
| HT-1080 (human fibrosarcoma cell) | 70 |
| Hepatocyte (normal human liver cell) | 430 |
| NHDF (normal human fibroblast cell) | 600 |
| BAE (normal bovine aorta vascular endothelial cell) | 9400 |

As shown in Table 5, apparently, the compound of Example 5 exerted a stronger activity for suppressing the growth of human-derived cancer cells than the activity for suppressing the growth of normal cell. The results clearly indicate that the compound of the invention is useful as an agent of suppressing cell growth.

Formulation Example 1

Tablet

Oral Tablet

In a 80-mg tablet formulation:

| | |
|---|---|
| Compound of Example 1: | 5.0 mg |
| Corn starch: | 46.6 mg |
| Crystalline cellulose: | 24.0 mg |
| Methyl cellulose: | 4.0 mg |
| Magnesium stearate: | 0.4 mg |

A mixture powder at the ratio is tableted and molded by a conventional method, to prepare an oral tablet.

Formulation Example 2

Tablet

Oral Tablet

In a 80-mg tablet formulation:

| | |
|---|---|
| Compound of Example 2: | 5.0 mg |
| Corn starch: | 46.6 mg |
| Crystalline cellulose: | 24.0 mg |
| Methyl cellulose: | 4.0 mg |
| Magnesium stearate: | 0.4 mg |

A mixture powder at the ratio is tableted and molded by a conventional method, to prepare an oral tablet.

INDUSTRIAL APPLICABILITY

Since the compound of the invention suppresses ICAM-1 expression, the compound of the invention is useful as an agent for inhibiting ICAM-1 expression, a therapeutic agent for inflammatory diseases, and an immunosuppressive agent. Furthermore, the compound of the invention is also useful as an agent for suppressing cell growth because the compound of the invention suppresses cell growth.

The invention claimed is:

1. An octahydronaphthalene compound represented by the following formula (1):

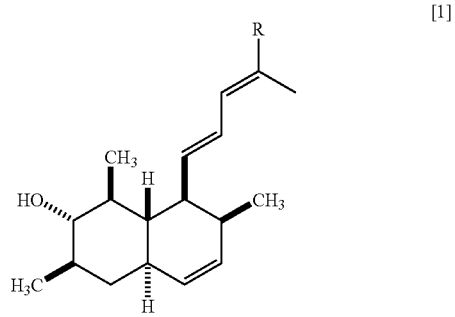

wherein R represents carboxy, hydroxymethyl, alkoxymethyl, alkoxycarbonyl, or —$CONR^1R^2$;

$R^1$ and $R^2$ are the same or different and each represents a hydrogen atom, phenyl, or an alkyl group and wherein said alkyl group may be substituted by:
1) 2-pyridyl;
2) 3-pyridyl; or
3) 4-pyridyl, or a pharmaceutically acceptable salt thereof.

2. The octahydronaphthalene compound according to claim 1, which is N-(pyridin-3-ylmethyl)-(2E,4E)-5-[(1S,2S,4aR,6R,7S,8S,8aS)-7-hydroxy-2,6,8-trimethyl-1,2,4a,5,6,7,8,8a-octahydronaphthalen-1-yl]-2-methylpenta-2,4-dienamide, or a pharmaceutically acceptable salt thereof.

3. A pharmaceutical composition, which comprises the octahydronaphthalene compound according to claim 1 or a pharmaceutically acceptable salt thereof, and a pharmaceutically acceptable carrier.

4. A method for treating a cancer chosen from the group consisting of lung, prostate, pancreas and fibrosarcoma, which comprises administering to a subject in need thereof an effective amount of the octahydronaphthalene compound according to claim 1 or a pharmaceutically acceptable salt thereof.

* * * * *